United States Patent [19]
Weissman et al.

[11] Patent Number: 6,114,150
[45] Date of Patent: *Sep. 5, 2000

[54] AMPLIFICATION OF NUCLEIC ACIDS

[75] Inventors: Sherman M. Weissman; Namadev Baskaran, both of New Haven, Conn.

[73] Assignee: Yale University, New Haven, Conn.

[*] Notice: This patent issued on a continued prosecution application filed under 37 CFR 1.53(d), and is subject to the twenty year patent term provisions of 35 U.S.C. 154(a)(2).

[21] Appl. No.: 08/758,662

[22] Filed: Dec. 2, 1996

Related U.S. Application Data

[63] Continuation-in-part of application No. 08/564,653, Nov. 29, 1995, abandoned.

[51] Int. Cl.$^7$ ...................................................... C12P 19/34
[52] U.S. Cl. ........................................ 435/91.2; 435/91.21
[58] Field of Search .............................. 435/91.2, 91.21, 435/6

[56] References Cited

U.S. PATENT DOCUMENTS

| | | | |
|---|---|---|---|
| 5,436,149 | 7/1995 | Barnes | 435/194 |
| 5,512,462 | 4/1996 | Cheng | 435/91.2 |
| 5,545,539 | 8/1996 | Miller | 435/91.2 |
| 5,545,540 | 8/1996 | Mian | 435/91.2 |
| 5,773,213 | 6/1998 | Gullans et al. | 435/6 |

OTHER PUBLICATIONS

Kuebler et al. (1995) Biochemica 4:28–9 (abstract).
Baskaran et al. (1996) Genome Methods 6:633–638.
Pomp et al. (1991) BioTechniques 10(1):58–59.
Barnes, Wayne M. (1994), "PCR Amplification of up to 35–kb DNA with High fidelity and High Yield from λ Bacteriophage Templates," *Proc. Natl. Acad. Sci. USA*, vol. 91, pp. 2216–2220.
Chong, Samuel S. et al. (1994), "Robust Amplification and Ethidium–Visible Detection of the Fragile X Syndrome CGG Repeat Using Pfu Polymerase," *American Journal of Medical Genetics* vol.51:522–526.
Rees, William A. et al. (1993), "Betaine Can Eliminate the Base Pair Composition Dependence of DNA Melting," *Biochemistry*, vol. 32:137–144.

*Primary Examiner*—Lisa B. Arthur
*Attorney, Agent, or Firm*—Morgan, Lewis & Bockius LLP

[57] ABSTRACT

Methods and compositions are provided to obtain uniform amplification of nucleic acid templates having varied G+C contents by adding betaine and DMSO to the reaction mixture.

35 Claims, 4 Drawing Sheets

Amplification of cDNAs from Small Number of Cells and Tissues:

AMPLIFICATION OF NUCLEIC ACIDS

CROSS-RELATED APPLICATIONS

This application is a continuation-in-part of U.S. application Ser. No. 08/564,653, filed Nov. 29, 1995, now abandoned.

TECHNICAL FIELD

The present invention relates generally to amplification of nucleic acids and, in particular, to amplification of G+C-rich templates.

BACKGROUND OF THE INVENTION

Amplification of nucleic acids has revolutionized molecular biology and is now one of the most rapid and versatile methods of producing large quantities of DNA for molecular analysis. Despite the power of this technique, uniform amplification of all templates, regardless of length or G+C content, remains a challenge. Amplification of longer nucleic acid fragments (up to 35 bp) has been accomplished by utilizing different enzymes selected for their thermal stability and editing functions (see PCR Methods and Applications 2:51, 257, 1993; Lundberg et al., Gene 108:1, 1991; Mattila et al., Nucleic Acids Res. 19:4967, 1991; Barnes, Proc. Natl. Acad. Sci. USA 91:2216, 1994; Cheng et al, Proc. Natl. Acad. Sci. USA 91:5695, 1994; Jeffreys et al., Nucleic Acids Res. 16:10953, 1988; Krishnan et al., Nucleic Acids Res. 19:6177, 1991; Maga and Richardson, Biotechniques 11:185, 1991; Rychlik et al., Nucleic Acids Res. 18:6409, 1990; and Kainz et al., Anal. Biochem. 202:46, 1992). However, templates with high G+C content, regardless of length, are only variably amplifiable or sometimes completely unamplifiable even in the presence of reagents that facilitate strand separation, stabilize the polymerase, or isostabilize DNA (e.g., dimethyl sulfoxide (DMSO), formamide, glycerol, or tetramethylammonium chloride (TMACl)) (Bookstein et al., Nucleic Acids Res. 18:1666, 1990; Sarkar et al., Nucleic Acids Res. 18:7465, 1990; Pomp and Medrano, Biotechniques 10:58, 1991; and Hung et al., Nucleic Acids Res. 18:4953, 1990).

Although the average G+C content of the human genome is about 40%, individual genes and genetic elements may have G+C content that is higher. For example, the human c-myc gene is 60% G+C with regions of greater of 70% G+C. As well, the majority of 5' ends of genes and promoters have regions that are G+C rich, and some diseases, such as Fragile X Syndrome, result from the in vivo expansion of G+C rich triplets (e.g., CGG for Fragile X Syndrome). Detection of these triplets in both normal and diseased individuals is difficult. Furthermore, the inability to uniformly amplify DNAs with high G+C content hinders other methods, such as quantitation of transcripts, gene mapping and sequence analysis.

In the present invention, compositions and methods are provided for amplifying nucleic acids regardless of their G+C content as well as providing other related advantages.

SUMMARY OF THE INVENTION

This invention generally provides methods and compositions for increasing the efficiency of amplification of nucleic acids, especially nucleic acids with high G+C content.

In one aspect, a reaction mixture is prepared by mixing nucleic acid templates, one or more primers, nucleotides, a first DNA polymerase and a second DNA polymerase that has 3' exonuclease activity, and adding to the reaction mixture a zwitterion and a compound that disrupts base pairing in an amount sufficient to increase amplification of an 80% G+C, 500 bp DNA fragment by two-fold, when the zwitterion and the compound are present as compared to when the zwitterion and the compound are absent. In a related aspect, the reaction mixture is prepared by mixing a homogeneous nucleic acid template, one or more primers, nucleotides, a first DNA polymerase and a second DNA polymerase that has 3' exonuclease activity, and adding to the reaction mixture a zwitterion or a compound that disrupts base pairings in an amount sufficient to increase amplification of an 80% G+C, 500 bp DNA fragment by two-fold, when the zwitterion or compound are present as compared to when the zwitterion or compound are absent.

In one embodiment, the first DNA polymerase lacks a 5' exonuclease activity. In a preferred embodiment, the first DNA polymerase is Klentaq1 DNA polymerase and the second DNA polymerase is Pfu DNA polymerase. In other embodiments, the DNA polymerase pairs are rTth DNA polymerase and Thermococcus litoralis DNA polymerase; Taq DNA polymerase and Pyrococcus DNA polymerase; Taq DNA polymerase and Pwo DNA polymerase.

In other embodiments, the zwitterion is selected from the group consisting of betaine, monomethyl glycine, dimethyl glycine, and D-carnitine. In yet another embodiment, the compound that disrupts base pairing is dimethylsulfoxide or formamide. In a preferred embodiment, the zwitterion is betaine and the compound is DMSO.

In yet other embodiments, the nucleic acid template is selected from the group consisting of genomic DNA, cDNA, plasmid DNA, DNA fragment, and viral DNA.

These and other aspects of the invention will become evident upon reference to the following detailed description and attached drawing. In addition, various references are set forth below which describe in more detail certain procedures or compositions. Each of these references are incorporated herein by reference in their entirety as if each were individually noted for incorporation.

SEQ ID No. 1 is a DNA sequence of the M13 forward primer.

SEQ ID No. 2 is a DNA sequence of the M13 reverse primer.

SEQ ID No. 3 is a DNA sequence of MHCcln1, which is derived from the MHC gene region.

SEQ ID No. 4 is a partial DNA sequence of human OCT-T1 cDNA.

SEQ ID No. 5 is a DNA sequence of human OCT1 cDNA.

SEQ ID No. 6 is a sequence of a primer used to amplify the repeat region of the Fragile X gene, FMR1.

SEQ ID No. 7 is a sequence of a primer used to amplify the repeat region of the Fragile X gene, FMR1.

SEQ ID No. 8 is a partial DNA sequence of TFR, the human transferrin receptor.

DETAILED DESCRIPTION OF THE INVENTION

Prior to setting forth the invention, it will be helpful to an understanding of the invention to define certain terms that are used hereinafter.

Nucleotides are depicted according to their recognized abbreviations, that is, "A" refers to adenine, "C" refers to cytosine, "G" refers to guanine, "T" refers to thymine, and "N" refers to either A or C or T or G.

As used herein, "amplification" refers to the increase in the number of copies of a particular nucleic acid fragment resulting from an enzymatic reaction, such as polymerase chain reaction, ligase chain reaction, or the like.

As used herein, "oligonucleotide" refers to a nucleic acid molecule comprising two or more deoxyribonucleotides or ribonucleotides, and preferably more than three. An oligonucleotide may be synthesized or produced by amplification or cloning.

As used herein, "polymerase chain reaction" or "PCR" refers to a particular process of amplification for the exponential amplification of a specific DNA fragment by utilizing two oligonucleotide primers that hybridize to opposite strands and flank the region of interest in a target DNA. The process consists of a repetitive series of cycles involving template denaturation, primer annealing, and the extension of the annealed primers by a DNA polymerase, such as the thermostable Taq DNA polymerase.

As used herein, a "primer" is an oligonucleotide that anneals to one strand of a nucleic acid template and allows elongation of a complementary strand by a polymerase.

As used herein, "template" refers to a sequence of nucleotides that can be copied by a DNA polymerase from a primer bound to the template.

As used herein, a "zwitterion" refers to a molecule that is a dipolar ion. At the isoelectric pI of the molecule, it will have no net charge; at a pH range between approximately the $K_a$ and the $K_b$, the molecule bears little net charge.

I. Amplification of nucleic acid templates

Amplification using thermostable enzymes generally involves multiple cycles of denaturation, annealing, and synthesis performed at different temperatures. An amplification reaction typically contains either heterogeneous or homogenous template nucleic acid, one or more oligonucleotide primers, nucleotides, various buffers and cofactors, and DNA polymerase. To amplify heterogeneous G+C rich templates, a zwitterion and compound that disrupts base pairing are added to the mix; if the template is homogeneous (e.g., plasmid clone DNA), either a zwitterion or compound is added.

Protocols vary somewhat in concentrations of reagents, temperatures, and incubation times, depending upon the apparatus, length of amplified product, enzyme used, and other parameters. Protocols are readily available (see, for example, manufacturer's instructions, Ausubel et al., *Current Protocols in Molecular Biology*, Greene Publishing, 1995; and Examples herein). Generally, a "hot-start" procedure is used, so that all reagents, save one, such as nucleotides, are mixed, and the temperature is raised to at least annealing temperature before the saved reagent is added. Amplification reactions may be analyzed by any of a variety of known methods. For example, the reaction may be electrophoresed in a polyacrylamide or agarose gel. The amplified material may be detected by staining with a dye, such as ethidium bromide, or by autoradiography if a radioactive label is incorporated.

II. Zwitterions and compounds that disrupt base pairing

As noted above, the present invention provides compositions comprising a zwitterion or dipolar ion in combination with a compound that disrupts base pairing to enhance and improve amplification of nucleic acids that are G+C rich. Typically, examples of G+C rich regions that show improvement of amplification in the present invention contain about 60% G+C over greater than 50 nucleotides, about 80% G+C in up to 500 nucleotide region, and 100% G+C in up to about 200 nucleotides.

A zwitterion contains both an acidic group and a basic group. The acidic group is associated and the basic group is dissociated at pH values between about the $pK_a$ (the pH at which the acidic group is half associated and half dissociated) and about the $pK_b$ (the pH at which the basic group is half associated and half dissociated). Dipolar ions are encountered, for example, whenever a molecule contains both an amino group and an acid group, providing that the amine is more basic than the anion of the acid. For example, all amino acids exist in a zwitterionic form between about pH 4 and about pH 9. Over this pH range, the amino acids bear little net charge, and at the isoelectric point, pI, bear no net charge.

The zwitterions for use in the present invention must have a basic group containing at least one alkyl group, which is preferably a methyl group. Preferably the basic group is an amine. A general formula for the zwitterion is thus:

wherein R is H, $CH_3$, $CH_2$—$CH_3$, or $(CH_2)_j$—$CH_3$, at least one R is not H, i is from 2 to about 6, and j is from 2 to about 6. Preferred zwitterions are betaine (trimethyl glycine), D-carnitine, dimethyl glycine, and monomethyl glycine.

For use in the present invention, the zwitterion should not inhibit DNA polymerases. It is preferable that the DNA polymerase retain at least 90% of activity at 2.5 M zwitterion concentration. The effect of the zwitterion on nucleic acid molecules is a decrease in the Tm of GC base pairs and an increase in the Tm of AT base pairs. The decrease or increase is preferably at least 2° C., at least 3° C., at least 4° C., and most preferably at least 5° C.

Compounds that disrupt base pairing (e.g., disrupt hydrogen bonding) include DMSO, formamide, sodium perchlorate, glyoxyl, and the like. Such compounds may be identified by their ability to lower the melting temperature of a nucleic acid duplex. Such compounds should not inhibit DNA polymerases. It is preferable that the DNA polymerase retain at least 90% of activity at a 10% compound concentration.

A zwitterion or a compound that disrupts base pairing can be tested for utility in the context of the present invention by demonstration of at least a two fold increase in the amount of amplified product from a homogeneous template of at least 80% G+C, in the presence of the zwitterion or compound as compared to the absence of the zwitterion or compound. When heterogeneous templates (i.e., multiple templates) are to be amplified, the zwitterion and compound that disrupts base pairing are tested in combination. The zwitterion and compound are added in amounts sufficient to cause an increase in efficiency of amplification. In general, the zwitterion is added from about 0.1 M to about 3 M, from about 0.5 M to about 4.5 M, or from about 1 M to about 2.5 M. In general, the compound is added from about 5% to about 15%, or preferably from about 5% to about 10%.

III. Two enzyme amplification systems

As noted above, an improvement in amplification is achieved when amplification is performed in a two-enzyme system.

Two-enzyme systems are used for amplification of long fragments. In general, one of the enzymes has a proofreading activity (3'→5' exonuclease) that corrects nucleotide misincorporations that may otherwise prematurely terminate DNA synthesis, and the other enzyme is highly processive. Preferably, one or both of the enzymes lack 5'→3' exonuclease activity. Also, preferably, the enzymes are thermostable. Examples of combinations of enzymes that are commonly used are Klentaq1 plus Pfu DNA polymerases (1:15 v/v), rTth plus Vent® isolated from *Thermococcus litoralis* DNA polymerases (Perkin-Elmer, Foster City, Calif.); Taq and Pyrococcus DNA polymerases (Life Technologies, Gaithersburg, Md.); and Taq and Pwo DNA polymerases (Boehringer-Mannheim, Indianapolis, Ind.). Other combinations may be used.

IV. Application of amplification of G+C rich templates

As described herein, the present invention provides compositions and methods for uniform amplification of nucleic acid templates regardless of G+C content. Such amplification allows accurate quantitation, detection of G+C rich regions, diagnosis of certain diseases, and improves construction of cDNA libraries, DNA sequence analysis, and the like. For example, 5' ends of genes are G+C rich and are often not amplified well during construction of a cDNA library. Some coding sequences are G+C rich and will also be underrepresented in a cDNA or genomic library. Without the present invention, if the starting material was a cDNA library with G+C-rich cDNA present in medium abundance (<0.1%), upon amplification, this G+C-rich nucleic acid would be less efficiently amplified and gradually lost. Thus, to find the cDNA in a screen by hybridization, several million clones would likely need to be examined. Using the present invention, the G+C rich cDNA should be present in the amplified material at the same level as in the starting material. Following amplification of cDNA from RNA isolated from a small number of cells, differential display amplification can be performed.

Moreover, several genetic diseases are caused by a natural expansion of a G+C-rich triplet. Such diseases include fragile X syndrome, spinobulbar muscular atrophy, myotonic dystrophy, Huntington's chonea, and spinocerebellar ataxia type 1.

Furthermore, in addition to enhancing amplification, the present invention may improve the efficiency of nucleic acid synthesis in general, including reverse transcription, in vitro transcription, primer extension and the like.

EXAMPLES

Example 1

Amplication of G+C Rich Templates Using Taq DNA Polymerase and Betaine or DMSO

A number of test DNAs are utilized in amplification reactions. Four of the test fragments are:

(i) a 2.7 kb cDNA encoding the octamer binding protein, OCT1 (GenBank accession No. X13403; Sturm et al., *Genes & Dev.* 2:1582, 1988; SEQ ID No. 8), which has a 52% G+C content;

(ii) a 1.6 kb fragment from the MHC region, MHCcln1, which has a 64% G+C content (see Shukla et al., *Nucleic Acids Res.* 19:4233, 1991; GenBank Accession No. L20433; SEQ ID No. 3, which presents nucleotides 320 to 850 of L20433);

(iii) a 0.8 kb fragment of human OCT-T1 cDNA, which encodes a transcription factor expressed in T lymphocytes that binds the octamer sequence, and which has an 80% G+C content (see Bhargava et al., *Proc. Natl. Acad. Sci. USA* 91:10260, 1993; SEQ ID NO. 4); and (iv) a 0.72 kb fragment of human transferrin receptor, TFR, which has a 44% G+C content (*Nature* 311:675, 1984; GenBank Accession No. X01060; SEQ ID No. 5, which presents nucleotides 352 to 866 of X01060).

As each of these fragments are cloned in pBluescript or a pUC plasmid (MHCcln1), primers for amplification of these fragments are the M13 forward primer (CGCCAGGGTTTTCCCAGTCACGAC; SEQ. ID No. 1) and the M13 reverse primer (AGCGGATAACAATTTCACACAGGA; SEQ ID No. 2). Thus, the sizes of the amplified fragments for each of these four templates, with the exception of MHCcln1, include 200 bp of multiple cloning sites of pBluescript vector.

The two G+C-rich templates are unsuccessfully amplified (MHCcln1 and OCT-T1) using AmpliTaq® DNA polymerase (Perkin-Elmer Cetus) under standard conditions. (See *Science* 239:487, 1988). The addition of DMSO (10% v/v), betaine (up to 2.5 M), glycerol (10% v/v), formamide (10% v/v) and TMACl (tetramethylammonium chloride) (0.1 mM to 1.0 M) or increasing annealing and denaturation temperatures did not result in visible amplification. In addition, betaine (>1.0 M), formamide (>5%), and TMACl (>100 mM) are inhibitory for amplification of the non-G+C-rich template OCT1.

Example 2

Amplification of G+C Rich Templates Using a Two Enzyme DNA Polymerase System and Betaine or DMSO

Each of the G+C-rich templates is set up in an amplification reaction using a two enzyme mixture, with and without the addition of betaine (0.5 to 2.5 M), DMSO (5–10%), formamide (5–10%/), glycerol (5–10%), TMACl (0.1 mM to 1 M), and tetramethylammonium acetate (TMAA) (0.1 mM–1.0 M).

The amplification reaction (50 μl) is performed in 20 mM Tris-HCl, pH 9.0 at 25° C., containing 150 μg/ml of bovine serum albumin, 16 mM ammonium sulfate 2.5 mM magnesium chloride, 200 μM of each dNTP, 50 ng each of the M13 forward primer and the M13 reverse primer, 0.5–1.0 ng of plasmid templates and 0.2–0.4 μl of Klentaq LA16 (a 1:15 v/v ratio of Klentaq1 (Ab Peptides Inc., St. Louis, Mo.), which is Taq DNA polymerase lacking the 5' to 3' exonuclease activity, and Pfu DNA polymerase (Stratagene, LaJolla, Calif.); the long and accurate (LA) system described in Barnes, *Proc. Natl. Acad. Sci. USA* 91:2216, 1994). DMSO, TMACl, TMAA, betaine, or the combination of DMSO and betaine is added to aliquots of the same mixture without dNTPs and overlaid with mineral oil. Amplification is performed in a thermocycler instrument using thin-walled tubes (0.5 ml). The tubes are heated at 95° C. for 15 seconds and amplification is initiated by the addition of dNTPs at 80° C. The following cycling conditions are used for 25 cycles: denaturation at 94° C. for 15 seconds, annealing at 50 to 55° C. for 1 minute, and extension at 68° C. for 5 minutes. Following amplification, 10 μl of the resulting product is loaded onto a 1% agarose gel (see *Molecular Cloning: A Laboratory Manual* by J. Sambrook et al., Cold Spring Harbor, 1989). The amplified DNA is stained with ethidium bromide and the gel is photographed while UV-irradiated by a transilluminator.

Figure 1A:
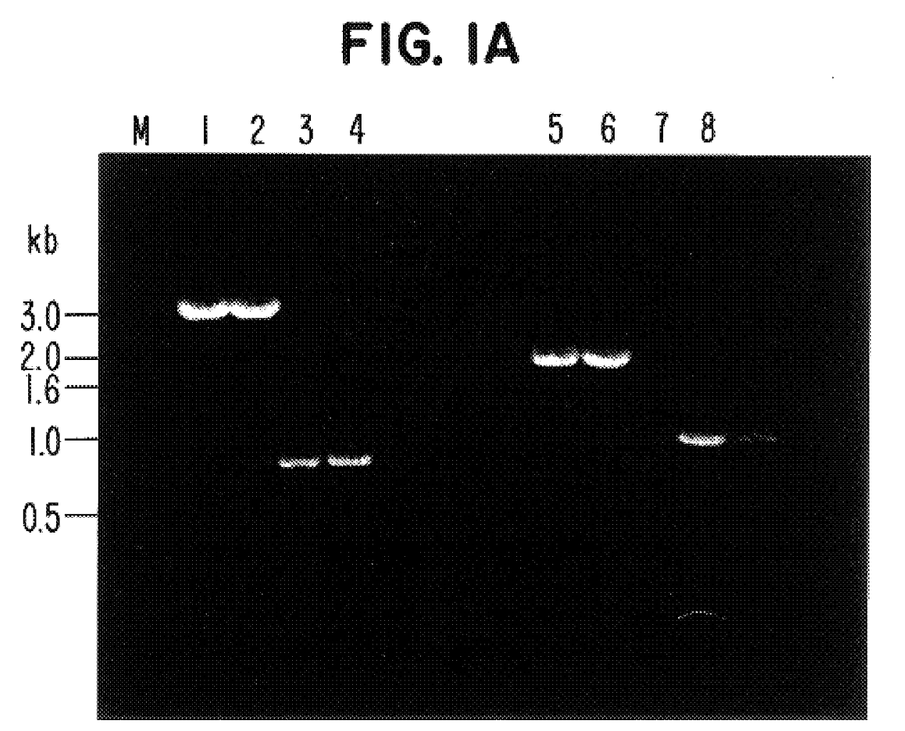
FIGS. 1A and 1B are photomicrographs depicting the electrophoretic screening data for the various test fragments and test solutions according to the present invention.
Figure 1B:
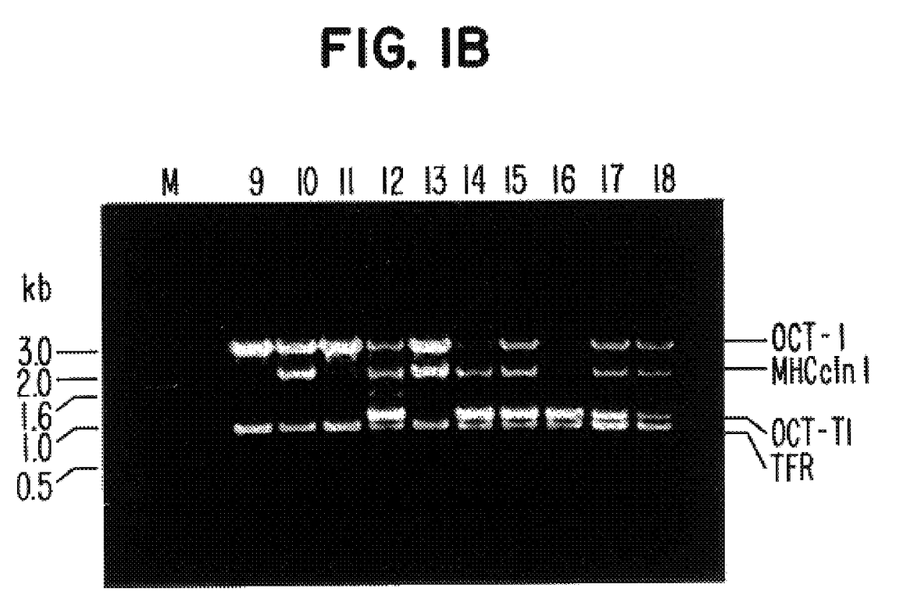

The results are shown in FIGS. 1A and 1B. The individual numbered lanes in FIGS. 1A and 1B, contain the template and additives listed in the following table.

TABLE 1

| Lane | Template* | Additive | Lane | Template | Additive |
|---|---|---|---|---|---|
| 1 | OCT1 | 2.2 M betaine | 10 | all four | 10% DMSO |
| 2 | OCT1 | 10% DMSO | 11 | all four | 1.1 M betaine |
| 3 | TFR | 2.2 M betaine | 12 | all four | 2.2 M betaine |
| 4 | TFR | 10% DMSO | 13 | all four | 5% DMSO + 1.1 M betaine |
| 5 | MHCclnl | 2.2 M betaine | 14 | all four | 5% DMSO + 2.2 M betaine |
| 6 | MHCclnl | 10% DMSO | 15 | all four | 10% DMSO + 1.1 M betaine |
| 7 | OCT-T1 | 2.2 M betaine | 16 | all four | 10% DMSO + 2.2 M betaine |
| 8 | OCT-T1 | 10% DMSO | 17 | all four | 7% DMSO + 1.0 M betaine |
| 9 | all four | 5% DMSO | 18 | all four | 5% DMSO + 1.4 M betaine |

*"all four" refers to the mixture of the 4 templates, OCT1, OCT-T1, TFR and MHCclnl.

As shown in FIG. 1A, each of the templates could be amplified in the presence of betaine or DMSO. Furthermore, DMSO and betaine do not have a negative effect on amplification. In contrast, the addition of tetramethylammonium chloride (TMACl), which is also a tetraalkylammonium ion, does not have a similar effect as that found with betaine. Moreover, TMACl and TMAA (at 0.1–1.0 M) inhibit amplification of OCT1. The addition of betaine and/or DMSO aids in the amplification of G+C-rich templates (lanes 5–8, FIG. 1A), while not having any adverse effect on the amplification of the other templates (lanes 1–4, FIG. 1A).

Amplification is also performed on a mixture of the four templates, varying the concentrations of DMSO and/or betaine. As can be seen in FIG. 1B, the four templates are not amplified uniformly upon addition of either DMSO or betaine alone (lanes 9–12). All the templates were amplified to a varying extent in the presence of 2.2 M betaine (lane 12), 5% DMSO +2.2 M betaine (lane 14), or 10% DMSO +1.1 betaine (lane 5). When 7% DMSO with 1.0 M betaine and 5% DMSO in combination with 1.4 M betaine (lanes 17 and 18) were tested, all templates were amplified uniformly. Thus, by adding both DMSO and betaine, preferably within a range of 1.0 M betaine with 6–8% DMSO or 5% DMSO with 1.2–1.8 M betaine, all four templates are amplified.

Thus, approximately equimolar amplification of all the templates occurred at 1.0 M betaine +7% DMSO (lane 17), and 5% DMSO +1.4 M betaine (lane 18). A combination of 1.0 M betaine with 6–8% DMSO or 5% DMSO with 1.2–1.8 M betaine resulted in similar uniform amplifications; accordingly such concentrations are preferred. Although at a higher concentration of DMSO (12–15%) or betaine (1.8–2.5 M), all the templates showed variable amplification, approximately equimolar yield of individual components of the template mixtures were obtained when DMSO and betaine were within the preferred concentration range and were combined with the LA system.

Example 3

Amplification of Templates Using Two Enzyme DNA Polymerase Systems and Betaine or DMSO Various single and two enzyme systems were used to amplify OCT-T1 (80% G+C) or TFR (44% G+C) templates. Amplification reactions were performed as above in the presence of 2 M betaine. The results are presented below.

TABLE 2

| Enzyme System | Enzymes | OCT-T1 (80% G + C) | TFR (44% G + C) | Sensitivity to Betaine |
|---|---|---|---|---|
| LA-16 | Klentaq1 and Pfu DNA Polymerase | +++ | +++ | − |
| AmpliTaq ® DNA Polymerase | rTaq DNA Polymerase | −/+ | +++ | + |
| XL PCR (Perkin-Elmer) | rTth and T. litoralis DNA Polymerase | +++ | +++ | − |
| Elongase (BRL) | Taq and Pyrococcus DNA Polymerase | +++ | +++ | − |
| Expand System (Boehringer Mannheim) | Taq and Pwo DNA Polymerase | ++ | +++ | − |
| Vent ® DNA Polymerase (NE Biolabs) | T. litoralis Polymerase | − | +++ | + |
| Deep Vent ™ Polymerase (NE Biolabs) | Pyrococcus Polymerase | − | − | + |

As shown above, all enzymes, except Pyrococcus polymerase, amplified TFR, a template with average G+C content. However, only the two enzyme systems were able to amplify OCT-T1, a template with high G+C content.

Example 4

Amplification of Templates Using Structural Analogues of Betaine

Various analogues of betaine and two tetraalkylammonium salts are used to amplify OCT-T1 or TFR templates. Amplification reactions are performed as above in the presence of either 2 M analogue or at least 0.15 M salt. Results are presented in the Table below.

TABLE 3

| Compound | OCT-T1 | TFR |
|---|---|---|
| Monomethyl glycine (2 M) | −/+ | +++ |
| Dimethyl glycine (2 M) | + | +++ |
| Glycine betaine (2 M) | +++ | +++ |
| D-carnitine (2 M) | +++ | +++ |

TABLE 3-continued

| Compound | OCT-T1 | TFR |
|---|---|---|
| TMAC (>0.15 M) | – | |
| TMAA (>0.15 M) | – | – |

The structure of the compounds is shown below.

TABLE 4

| | |
|---|---|
| Glycine betaine | $(CH_3)_3\overset{+}{N}-CH_2-COO^-$ |
| D-carnitine | $^-OOC-CH_2-\overset{OH}{\underset{\|}{CH}}-CH_2-\overset{+}{N}-(CH_3)_3$ |
| Monomethyl glycine | $CH_3-H_2\overset{+}{N}-CH_2-COO^-$ |
| Dimethyl glycine | $(CH_3)_2-\overset{+}{NH}-CH_2-COO^-$ |
| TMACl | $(CH_3)_4-\overset{+}{N}-Cl^-$ |
| TMAA | $(CH_3)_4-\overset{+}{N}-CH_2COO^-$ |

As shown in the table, TMACl and TMAA are unable to facilitate amplification of either template and most likely inhibit the enzyme. However, the zwitterions facilitated amplification of both templates, the quarternary ammonium ions working best.

Example 5

Amplification of G+C Rich Repeats of the Fragile X Gene

Amplification of the G+C-rich repeat expansion involved in Fragile X Syndrome is performed. Fragile X Syndrome is one of the most common causes of mental retardation affecting 1 in 1,500 males, and 1 in 2,500 females. The fragile X site has been mapped to Xq27.3, and shown to be due to the expansion of CGG triplet repeats in the 5'-end of the FMR1 gene. Normal subjects have 2–50 CGG repeats with an average at 29 repeats, those with premutation have about 50–200 repeats, and individuals with disease have more than 200 repeats (i.e., a full mutation) (see Nussbaum and Ledbetter, *Ann. Rev. Genetics* 20:109, 1986; Verkerk et al., *Cell* 65:905, 1991; and Kremer et al., *Science* 252:1711, 1991). Diagnostic confirmation of this disease has primarily been accomplished by cytogenetic analysis of the cells and Southern blotting of the DNA from these patients (see Sutherland, *Am. J. Hum. Genet.* 31:125, 1979; and Rousseau et al., *N. Engl. J. Med.* 325:1673, 1991). The sequence of the fragile X CGG repeat region may be found in GenBank accession No. X61378.gb-pr, and encompasses nucleotides 2599 to 2868.

The methods described herein are used to amplify the G+C-rich fragile X CGG triplet repeat region (85% G+C) directly from genomic DNA of a cell line with a normal FMR1 gene, JV, (29 CGG repeat), genomic DNA from 2 males with premutations (74 and 119 CGG repeats, respectively), and genomic DNA from 2 patients carrying full mutations (>1000 CGG repeats). The sizes of the CGG repeats were obtained by Southern blotting and hybridization with specific probes.

Amplification is performed as described above in the presence of 10% DMSO+1.1 M betaine or 5% DMSO+2.0 M betaine. The sequence of primers used are:

primer c: GCTCAGCTCC GTTCGGTTT CACTTC-CGGT (SEQ ID No. 6)

primer f: AGCCCCGCAC TTCCACCACC AGCTC-CTCCA (SEQ ID No. 7)

Either 10 or 100 ng of genomic DNA from each sample is mixed in 20 mM Tris-Cl (pH 9.0) containing 150 µg/ml bovine serum albumin, 16 mM ammonium sulfate, 2.5 mM magnesium chloride, and 50 ng of each primer. All the components, except dNTP, are denatured at 94° C. for 15 sec, and dNTPs are added at 80° C. Amplification proceeded using the following cycling conditions for 40 cycles: denaturation at 94° C. for 15 sec, annealing at 65° C. for 1 minute, and extension at 68° C. for 5 min (or annealing and extension was alternatively done at 68° C. for 5 min). Following amplification, 10 µl of the reaction was loaded on a 2% agarose gel and the bands visualized by ethidium bromide staining.

Figure 2:
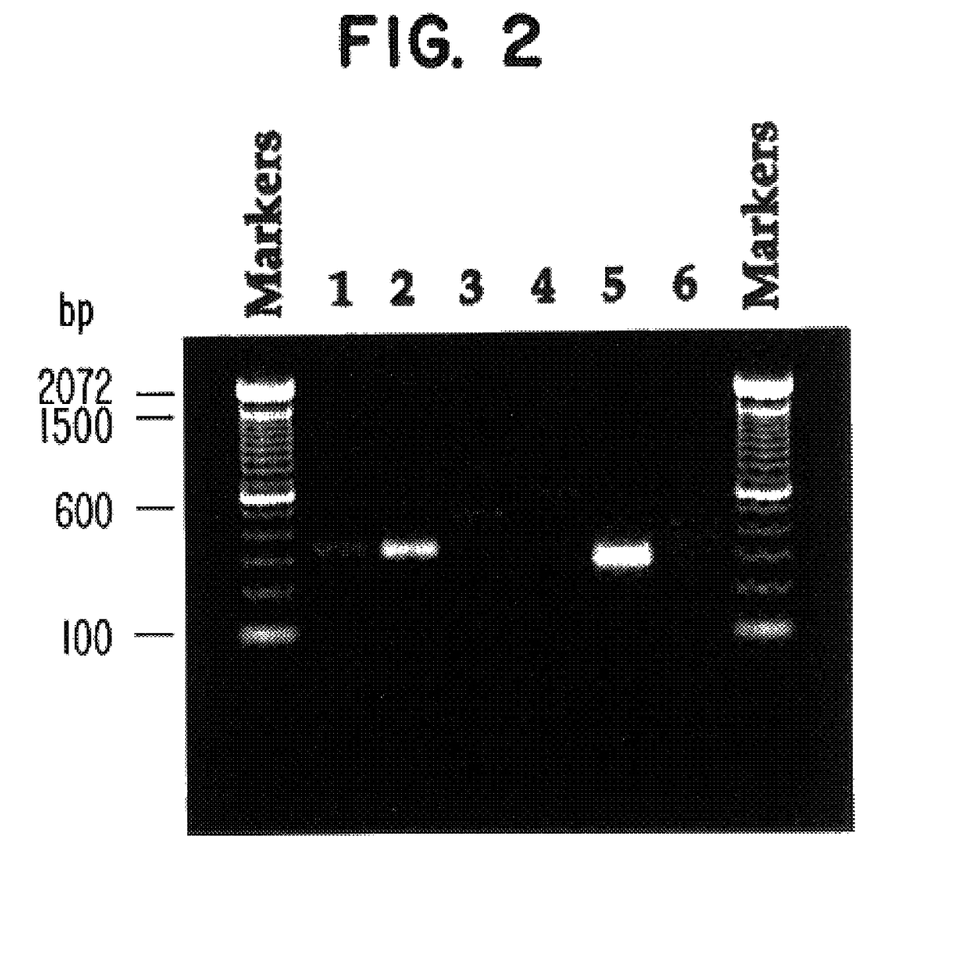
FIG. 2 is a photomicrograph depicting the electrophoretic screening data for the amplification of the CGG triplet repeat in Fragile X Syndrome.

The results are depicted in FIG. 2, in which lane 1 is JY DNA (10 ng); lane 2 is JY DNA (100 ng); lane 3 is 74 CGG repeat containing DNA; lane 4 is 119 CGG repeats containing DNA; lane 5 is DNA containing heterozygous full mutation in a female patient; and lane 6 is a full mutation from a male DNA sample.

An approximately 300 bp PCR product is observed for JY (FIG. 2, lanes 1 and 2), and the expected size fragments for 74 repeat (440 bp) and 119 repeats (575 bp) are observed as well (FIG. 2, lanes 3 and 4). However, no specific band is observed for the DNA from a male patient carrying a full mutation (FIG. 2, lane 6), and only a normal band (300 bp) is observed for DNA from a female patient carrying a full mutation as well as a normal gene (FIG. 2, lane 5). Thus, the normal sized repeat (with an average repeat number of 29) and remutation expansion can be visibly amplified, whereas the full mutation (>200 repeat) is not visibly amplified.

Example 6

Amplification of cDNAs as Using Betaine or DMSO

First strand cDNAs synthesized from total RNA isolated from a small number of cells and tissues are amplified. Either Jurkat T cells, induced for 4 hrs with 50 nM phorbol 12-myristate 13-acetate and 2 µg/ml phytohemagglutinin, or human inner ear samples, obtained during a surgical procedure, were used. Total RNA was isolated, and double-stranded cDNA was made. An adaptor containing a NotI site was ligated to the cDNAs. Amplification reactions are performed as described above using Klentaq LA16, using the adaptor as primer in the presence of 1.5 M betaine and 7% DMSO, except that each cycle consisted of denaturation at 95° C. for 15 sec, annealing at 55° C. for 1 min, and extension at 68° C. for 5 min. A second round of amplification was performed on 1 µl of reaction mix using the cycle conditions: denaturation at 95° C. for 15 sec, annealing at 60° C. for 1 min, and extension at 68° C. for 5 min.

Figure 3:
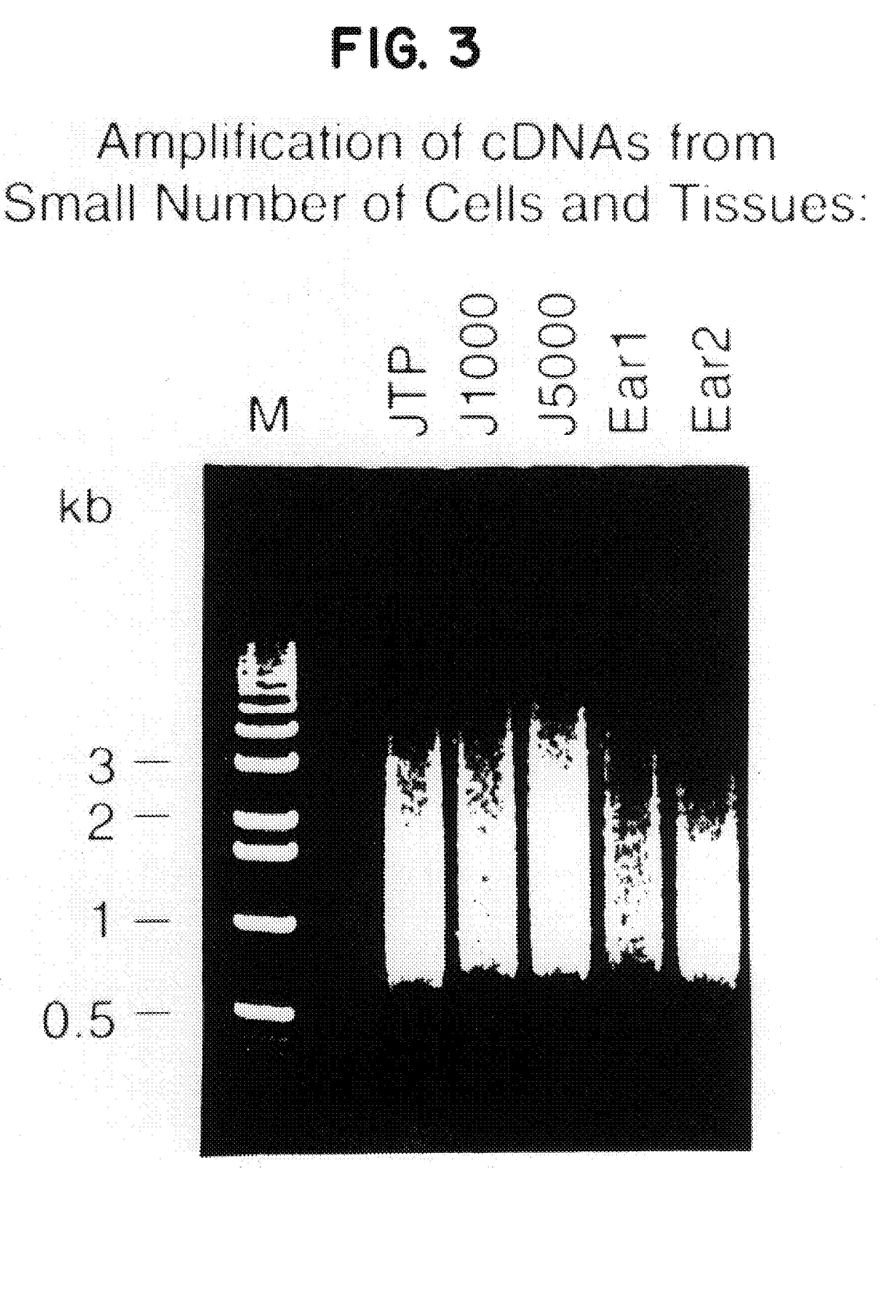
FIG. 3 is a photograph of amplification of cDNAs from a small number of cells and tissues. M, molecular weight markers; JTP, cDNA from activated Jurkat T cells; J1000, cDNA from 1000 Jurkat cells; J5000, cDNA from 5000 Jurkat cells; Ear1, cDNA from human inner ear; Ear2, cDNA from human inner ear.

As shown in FIG. 3, uniform amplification occurred using cDNA from tissues (Ear1 and Ear2) as well as from cell lines (JTP, 11000, J5000). Moreover, even when small numbers of cells are used to extract total RNA, amplification is substantial (lanes J1000, J5000).

It will be appreciated that, although specific embodiments of the invention have been described herein for purposes of illustration, various modifications may be made without departing from the spirit and scope of the invention. Accordingly, the invention is not limited except as by the appended claims.

We claim:

1. A method for uniformly amplifying a heterogeneous mixture of nucleic acid templates regardless of G+C content, comprising the steps of:
   (a) providing a reaction mixture comprising a heterogeneous mixture of nucleic acid templates of varying G+C content; and
   (b) adding to the reaction mixture betaine and DMSO in an amount sufficient to uniformly amplify the heterogeneous mixture of templates regardless of G+C content, wherein said amount of betaine and DMSO is selected from the group consisting of (i) about 1.0 M betaine with about 6–8% DMSO and (ii) about 1.2M–1.8M betaine with about 5% DMSO.

2. The method of claim 1, wherein the heterogeneous mixture of nucleic acid templates contains templates comprising 60% G+C over greater than 50 nucleotides, 80% G+C in up to about 500 nucleotides or 100% G+C in up to about 200 nucleotides.

3. The method of claim 1, wherein the heterogeneous mixture of nucleic acid templates is a cDNA library.

4. The method of claim 3, wherein the cDNA library contains G+C rich cDNA.

5. The method of claim 4, wherein the G+C rich cDNA is efficiently amplified.

6. The method of claim 4, wherein G+C rich cDNA is present after amplification at the same ratio to other templates as in the original cDNA library.

7. The method of any one of claims 1–6, wherein the reaction mixture contains a first DNA polymerase and a second DNA polymerase.

8. The method of claim 7, wherein the first DNA polymerase lacks 5'→3' exonuclease activity.

9. The method of claim 7, wherein the first DNA polymerase is Taq DNA polymerase that lacks 5'→3' exonuclease activity and the second DNA polymerase is Pfu DNA polymerase.

10. The method of claim 7, wherein the first DNA polymerase is rTth DNA polymerase and the second DNA polymerase is *Thermococcus litoralis* DNA polymerase.

11. The method of claim 7, wherein the first DNA polymerase is Taq DNA polymerase and the second DNA polymerase is Pyrococcus DNA polymerase.

12. The method of claim 7, wherein the first DNA polymerase is rTaq DNA polymerase and the second DNA polymerase is Pwo DNA polymerase.

13. The method of any one of claims 1–7, wherein the reaction mixture after step (b) comprises about 1.0 M betaine and about 6–8% DMSO.

14. The method of any one of claims 1–7, wherein the reaction mixture after step (b) comprises about 1.2M–1.8M betaine and about 5% DMSO.

15. The method of claim 1, wherein the mixture of nucleic acid templates of varying G+C content is selected from the group consisting of genomic DNA, cDNA, plasmid DNA, DNA fragments, and viral DNA.

16. The method of either of claims 1 or 3, wherein an adaptor is added to the ends of the mixture of nucleic acid templates of varying G+C content before amplification.

17. A method for uniformly amplifying a cDNA library, comprising the steps of:
(a) providing a reaction mixture comprising cDNA prepared from mRNA from a cell or tissue source; and
(b) adding to the reaction mixture betaine and DMSO in an amount sufficient to uniformly amplify the cDNA library, wherein said amount of betaine and DMSO added is selected from the group consisting of (i) about 1.0 M betaine with about 6–8% DMSO and (ii) about 1.2M–1.8M betaine with about 5% DMSO.

18. The method of claim 17, wherein the cDNA library is uniformly amplified regardless of G+C content of the individual cDNAs.

19. The method of claim 18, wherein the cDNA library contains G+C rich cDNA in an abundance of less than about 0.1%.

20. The method of claim 17, wherein the reaction mixture contains a first DNA polymerase and a second DNA polymerase.

21. The method of claim 20, wherein the first DNA polymerase lacks 5'→3' exonuclease activity.

22. The method of claim 21 wherein the first DNA polymerase is Taq DNA polymerase that lacks 5'→3' exonuclease activity and the second DNA polymerase is Pfu DNA polymerase.

23. The method of claim 17, wherein the reaction mixture after step (b) comprises about 1.0 M betaine and about 6–8% DMSO.

24. The method of claim 17, wherein the reaction mixture after step (b) comprises about 1.2M–1.8M betaine and about 5% DMSO.

25. The method of any one of claims 17–24, wherein an adaptor is added to the ends of the cDNA before amplification.

26. A method of differential display amplification, comprising the steps of:
(a) providing a reaction mixture comprising cDNA prepared from mRNA from a cell or tissue source; and
(b) adding to the reaction mixture betaine and DMSO in an amount sufficient to uniformly amplify the cDNA library wherein said amount of betaine and DMSO added is selected from the soup consisting of (i) about 1.0M betaine with about 6–8% DMSO and (ii) about 1.2M–1.8M betaine with about 5% DMSO.

27. The method of claim 26, wherein the cDNA is uniformly amplified regardless of G+C content of the individual cDNAs.

28. The method of claim 26, wherein the reaction mixture contains a first DNA polymerase and a second DNA polymerase.

29. The method of claim 28, wherein the first DNA polymerase lacks 5'→3' exonuclease activity.

30. The method of claim 29 wherein the first DNA polymerase is Taq DNA polymerase that lacks 5'→3' exonuclease activity and the second DNA polymerase is Pfu DNA polymerase.

31. The method of claim 26, wherein the reaction mixture after step (b) comprises about 1.0M betaine and about 6–8% DMSO.

32. The method of claim 26, wherein the reaction mixture after step (b) comprises about 1.2M–1.8M betaine and about 5% DMSO.

33. The method of any one of claims 26–32, wherein an adaptor is added to the ends of the cDNA before amplification.

34. The method of any one of claims 1, 17 or 26, further comprising the step of:
(c) uniformly amplifying substantially all of the templates present in the reaction mixture regardless of the G+C content of individual templates.

35. The method of claim 34, wherein the reaction mixture contains templates comprising 80% G+C content.

* * * * *

UNITED STATES PATENT AND TRADEMARK OFFICE
CERTIFICATE OF CORRECTION

PATENT NO. : 6,114,150
DATED : September 5, 2000
INVENTOR(S) : Sherman M. Weissman et al.

It is certified that error appears in the above-identified patent and that said Letters Patent is hereby corrected as shown below:

Column 1,
Line 7, insert the following:
-- U.S. GOVERNMENT SUPPORT
This work was supported by a grant from the National Institutes of Health (CA-42556). --

Signed and Sealed this

Twenty-eighth Day of December, 2004

JON W. DUDAS
*Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (xi) SEQUENCE DESCRIPTION: SEQ ID NO:1:

CGCCAGGGTT TTCCCAGTCA CGAC                                               24

(2) INFORMATION FOR SEQ ID NO:2:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (xi) SEQUENCE DESCRIPTION: SEQ ID NO:2:

AGCGGATAAC AATTTCACAC AGGA                                               24

(2) INFORMATION FOR SEQ ID NO:3:

(i) SEQUENCE CHARACTERISTICS:
       (A) LENGTH: 1652 base pairs
       (B) TYPE: nucleic acid
       (C) STRANDEDNESS: single
       (D) TOPOLOGY: linear (xi) SEQUENCE DESCRIPTION: SEQ ID NO:3:

GGATCCGGCC CCACGGAGGT CCCCATCTCC CTCAAGATTC TCAGATTCAT CCCCAATGAG          60

TGGTGTAGCC CCTACAGGGG TGTCAGCCCC CCTCATCACC AACAGTGACA GTGACAGAGG         120

CTGGAGATGA GGGGCCAGCA GGCTCCAGGG AGTCGGGGGT GGCCTTGGGC AGGGTTTCTT         180

CACTACGAGG GGTGTTCCCC AAAGAGCCAT GAACTGTAGA GGAAGAGAAA AAGTTCAGAG         240

CTAAGGGCTC AGGAGATCCT GTGTATTTAG GGAAGGTGAC GGTCCAATTG GGGCCCGTTT         300

TAGCTGCACT CACCTCTCTC GGTGGCTCCT CTGGTTTCCT TCTCCAGCAG CTCCCCCATC         360

TCAGCGGGGG CCATCCCCCT GGGAGGGGAG ACAAGGGACA GGAGGGCTGG TCAGCCCAGT         420

AGAGAGTTGG GGGGTCCAGG ATGCCTGGGC CCTGGGAAGA GAGAGTAGGC TCCGGGGCCT         480

ACCTCTTCCT CTGGCCCTTC CGCGGCCTCG GCTGCCCGGA GCCGCACAAC CCTCCCCGGG         540

CCGCATAATC CCTCCTTGAT GACCCTCCCT CTCGGTAGTA CCCGCACTCT GGGGCCGAGA         600

GAAGAGGAGG GGGCACGGAC TCTTGGGGGG GGCCTCCGAG CCCGGCCCCG CCCCTCTCCC         660

CGGCTGCACG CGCCGATACC CTTTGTACCC AGGCGCGGGA CCCGGACAAT CCTCAGATCC         720

TCCAGCACCC GCTGCCCCCC AGCCCGGTGG ACGGCCCCTC GTGCCCCTCA CGCGTGCTCC         780

TGGGGCCCCG GCGCCCGTCG CCCAGTGCGG GCAGGCCGGC GGCTGCACGC GCGCCTCCGT         840

GCCCACTCCC CCCACCTCCC ACACCCTGGT CCCCTCATCC GCCCCGGTG CTGGCCCCCT          900

GGATTGCTGC AAGTCCCGCC CGGCCCCCGG CCCCGTTGCA CCCCCGGAGC ATTGCACGGC         960

GCTTCCCCCG GGGGCGCGCG CGGGCATGCA CCCGCCTCTC CCCCTCCCTT CCGCACCTCG        1020

GCGGCCGCCG CCGCTGCAGC TCCCGCCGCC GCCGCCATCG CGCTTGCGCT GGGGGCCGAG        1080

```
CCGGCGCGCG GCCGCCCCGG GTCACGTGGG CGAGGGAGGG AGGGCGAGGA GGAGCCTTAA      1140

AGGAGCCGCT ACATGCTTTT TGGCCATTTT CCCCTGAGAG CGGCCTCGGA GATGGCTGTG      1200

ACTGTCCTAA GCTGGGAGCT GCAAGGGAGA ATTCCTGTCA TTCCTGGCCT CAGTTCTGCA      1260

GGGACCGAGG GCGAGACACG CCTGGGCCCA GGTGTGGCGT CTCTGTCCCC ATCTGGTTTT      1320

AGGTAACAAG CGGACGTTCT GAACTTCTCG GCTCTCGGCA GCGGCTGTAT TTCCTCTGGC      1380

CTGGTTGGGC TTTTCCCGCC TCTGGTTGCT TTTCTGCCTT TCTAGTTTTT GGGTTACCAG      1440

ATAGAAGGCT TGGCCTCAGT TTTGGCCTCG CCTTTTTGCT CTTTCTAACG AGCACGAAGG      1500

GGCGATAGGG ACGCGGAGGA CACCTTTATT CTTGGCTGGT TCTAGCATGC TGCTTCATGT      1560

CCCCTGGAGC AGCGTGCCCT TCTGAAAACC TGTGGCTAAA TGTCTCTTCT GTTTATATCT      1620

GGCGTGTTAC ACCTTCACAC GCACTAGGAT CC                                    1652
```

(2) INFORMATION FOR SEQ ID NO:4:

(i) SEQUENCE CHARACTERISTICS:
        (A) LENGTH: 530 base pairs
        (B) TYPE: nucleic acid
        (C) STRANDEDNESS: single
        (D) TOPOLOGY: linear     (xi) SEQUENCE DESCRIPTION: SEQ ID NO:4:

```
CGAGGCCATC CGGCGGGCCT GCCTGCCCAC GCCGCCGCTG CAGAGCAACC TCTTCGCCAG       60

CCTGGACGAG ACGCTGCTGG CGCGGGCCGA GGCGCTGGCG GCCGTGGACA TCGCCGTGTC      120

CCAGGGCAAG AGCCATCCTT TCAAGCCGGA CGCCACGTAC CACACGATGA ACAGCGTGCC      180

GTGCACGTCC ACTTCCACGG TGCCTCTGGC GCACCACCAC CACCACCACC ACCACCACCA      240

GGCGCTCGAA CCCGGCGATC TGCTGGACCA CATCTCCTCG CCGTCGCTCG CGCTCATGGC      300

CGGCGCGGGC GGCGCGGGCG CGGCGGCCGG CGGCGGCGGC GCCCACGACG GCCCGGGGGG      360

CGGTGGCGGC CCGGGCGGCG GCGGCGGCCC GGGCGGCGGC GGCCCCGGGG GAGGCGGCGG      420

TGGCGGCCCG GGGGCGGCG GCGGCGGCCC GGGCGGCGGG CTCCTGGGCG GCTCCGCGCA      480

CCCTCACCCG CATATGCACA GCCTGGGCCA CCTGTCGCAC CCCGCGGCGG                 530
```

(2) INFORMATION FOR SEQ ID NO:5:

(i) SEQUENCE CHARACTERISTICS:
        (A) LENGTH: 515 base pairs
        (B) TYPE: nucleic acid
        (C) STRANDEDNESS: single
        (D) TOPOLOGY: linear     (xi) SEQUENCE DESCRIPTION: SEQ ID NO:5:

```
ATGGCGATAA CAGTCATGTG GAGATGAAAC TTGCTGTAGA TGAAGAAGAA AATGCTGACA       60

ATAACACAAA GGCCAATGTC ACAAAACCAA AAAGGTGTAG TGGAAGTATC TGCTATGGGA      120

CTATTGCTGT GATCGTCTTT TTCTTGATTG GATTTATGAT TGGCTACTTG GGCTATTGTA      180

AAGGGGTAGA ACCAAAAACT GAGTGTGAGA GACTGGCAGG AACCGAGTCT CCAGTGAGGG      240

AGGAGCCAGG AGAGGACTTC CCTGCAGCAC GTCGCTTATA TTGGGATGAC CTGAAGAGAA      300

AGTTGTCGGA GAAACTGGAC AGCACAGACT TCACCAGCAC CATCAAGCTG CTGAATGAAA      360

ATTCATATGT CCCTCGTGAG GCTGGATCTC AAAAAGATGA AAATCTTGCG TTGTATGTTG      420

AAAATCAATT TCGTGAATTT AAACTCAGCA AAGTCTGGCG TGATCAACAT TTTGTTAAGA      480

TTCAGGTCAA AGACAGCGCT CAAAACTCGG TGATC                                 515
```

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (xi) SEQUENCE DESCRIPTION: SEQ ID NO:6:

```
GCTCAGCTCC GTTTCGGTTT CACTTCCGGT                                30
```

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear     (xi) SEQUENCE DESCRIPTION: SEQ ID NO:7:

```
AGCCCCGCAC TTCCACCACC AGCTCCTCCA                                30
```

(2) INFORMATION FOR SEQ ID NO:8:

(i) SEQUENCE CHARACTERISTICS:
        (A) LENGTH: 2584 base pairs
        (B) TYPE: nucleic acid
        (C) STRANDEDNESS: single
        (D) TOPOLOGY: linear     (xi) SEQUENCE DESCRIPTION: SEQ ID NO:8:

```
GAGGAGCAGC GAGTCAAGAT GAGAGTTCAG CCGCGGCGGC AGCAGCAGCA GACTCAAGAA     60
TGAACAATCC GTCAGAAACC AGTAAACCAT CTATGGAGAG TGGAGATGGC AACACAGGCA    120
CACAAACCAA TGGTCTGGAC TTTCAGAAGC AGCCTGTGCC TGTAGGAGGA GCAATCTCAA    180
CAGCCCAGGC GCAGGCTTTC CTTGGACATC TCCATCAGGT CCAACTCGCT GGAACAAGTT    240
TACAGGCTGC TGCTCAGTCT TTAAATGTAC AGTCTAAATC TAATGAAGAA TCGGGGGATT    300
CGCAGCAGCC AAGCCAGCCT TCCCAGCAGC CTTCAGTGCA GGCAGCCATT CCCCAGACCC    360
AGCTTATGCT AGCTGGAGGA CAGATAACTG GGCTTACTTT GACGCCTGCC CAGCAACAGT    420
TACTACTCCA GCAGGCACAG GCACAGGCAC AGCTGCTGGC TGCTGCAGTG CAGCAGCACT    480
CCGCCAGCCA GCAGCACAGT GCTGCTGGAG CCACCATCTC CGCCTCTGCT GCCACGCCCA    540
TGACGCAGAT CCCCCTGTCT CAGCCCATAC AGATCGCACA GGATCTTCAA CAACTGCAAC    600
AGCTTCAACA GCAGAATCTC AACCTGCAAC AGTTTGTGTT GGTGCATCCA ACCACCAATT    660
TGCAGCCAGC GCAGTTTATC ATCTCACAGA CGCCCCAGGG CCAGCAGGGT CTCCTGCAAG    720
CGCAAAATCT TCAAACGCAA CTACCTCAGC AAAGCCAAGC CAACCTCCTA CAGTCGCAGC    780
CAAGCATCAC CCTCACCTCC CAGCCAGCAA CCCCAACACG CACAATAGCA GCAACCCCAA    840
TTCAGACACT TCCACAGAGC CAGTCAACAC CAAAGCGAAT TGATACTCCC AGCTTGGAGG    900
AGCCCAGTGA CCTTGAGGAG CTTGAGCAGT TTGCCAAGAC CTTCAAACAA AGACGAATCA    960
AACTTGGATT CACTCAGGGT GATGTTGGGC TCGCTATGGG GAAACTATAT GGAAATGACT   1020
TCAGCCAAAC TACCATCTCT CGATTTGAAG CCTTGAACCT CAGCTTTAAG AACATGTGCA   1080
AGTTGAAGCC ACTTTTAGAG AAGTGGCTAA ATGATGCAGA GAACCTCTCA TCTGATTCGT   1140
CCCTCTCCAG CCCAAGTGCC CTGAATTCTC CAGGAATTGA GGGCTTGAGC CGTAGGAGGA   1200
AGAAACGCAC CAGCATAGAG ACCAACATCC GTGTGGCCTT AGAGAAGAGT TTCTTGGAGA   1260
```

-continued

```
ATCAAAAGCC TACCTCGGAA GAGATCACTA TGATTGCTGA TCAGCTCAAT ATGGAAAAAG    1320

AGGTGATTCG TGTTTGGTTC TGTAACCGCC GCCAGAAAGA AAAAAGAATC AACCCACCAA    1380

GCAGTGGTGG GACCAGCAGC TCACCTATTA AAGCAATTTT CCCCAGCCCA ACTTCACTGG    1440

TGGCGACCAC ACCAAGCCTT GTGACTAGCA GTGCAGCAAC TACCCTCACA GTCAGCCCTG    1500

TCCTCCCTCT GACCAGTGCT GCTGTGACGA ATCTTTCAGT TACAGGCACT TCAGACACCA    1560

CCTCCAACAA CACAGCAACC GTGATTTCCA CAGCGCCTCC AGCTTCCTCA GCAGTCACGT    1620

CCCCCTCTCT GAGTCCCTCC CCTTCTGCCT CAGCCTCCAC CTCCGAGGCA TCCAGTGCCA    1680

GTGAGACCAG CACAACACAG ACCACCTCCA CTCCTTTGTC CTCCCCTCTT GGGACCAGCC    1740

AGGTGATGGT GACAGCATCA GGTTTGCAAA CAGCAGCAGC TGCTGCCCTT CAAGGAGCTG    1800

CACAGTTGCC AGCAAATGCC AGTCTTGCTG CCATGGCAGC TGCTGCAGGA CTAAACCCAA    1860

GCCTGATGGC ACCCTCACAG TTTGCGGCTG GAGGTGCCTT ACTCAGTCTG AATCCAGGGA    1920

CCCTGAGCGG TGCTCTCAGC CCAGCTCTAA TGAGCAACAG TACACTGGCA ACTATTCAAG    1980

CTCTTGCTTC TGGTGGCTCT CTTCCAATAA CATCACTTGA TGCAACTGGG AACCTGGTAT    2040

TTGCCAATGC GGGAGGAGCC CCCAACATCG TGACTGCCCC TCTGTTCCTG AACCCTCAGA    2100

ACCTCTCTCT GCTCACCAGC AACCCTGTTA GCTTGGTCTC TGCCGCCGCA GCATCTGCAG    2160

GGAACTCTGC ACCTGTAGCC AGCCTTCACG CCACCTCCAC CTCTGCTGAG TCCATCCAGA    2220

ACTCTCTCTT CACAGTGGCC TCTGCCAGCG GGGCTGCGTC CACCACCACC ACCGCCTCCA    2280

AGGCACAGTG AGCTGGGCAG AGCTGGGCTG CCAGAAGCCT TTTTCACTCT GCAGTGTGAT    2340

TGGACTGCCA GCCAGGTTAA TAAACTGAAA AATGTGATTG GCTTCCTCTC GCCGTGTTGT    2400

GAGGGCAAAG GAGAGAAGGG AGAAAAAAAA AAAAAAACC ACACACACCC ATACACAATA    2460

TACCAGAAAA GGAAGGAAGG ATGGAGACGG AACATTTGCC TAATTTGTAA TAAAACACTG    2520

TCTTTTCAGG GTTGCTTCAT GGGTTGGAGG ACTTTCTAAC CAAAAATTAA AAAAAAAAA    2580

AAAA                                                                2584
```